United States Patent [19]

Sakai et al.

[11] Patent Number: 4,989,454
[45] Date of Patent: Feb. 5, 1991

[54] SCANNING APPARATUS FOR A SCANNING MICROSCOPE

[75] Inventors: Mitsugu Sakai, Hachioji; Koichi Karaki, Hino; Yasuo Sasaki, Hachioji, all of Japan

[73] Assignee: Olympus Optical Co., Ltd., Tokyo, Japan

[21] Appl. No.: 564,655

[22] Filed: Aug. 9, 1990

Related U.S. Application Data

[63] Continuation of Ser. No. 365,149, Jun. 12, 1989, abandoned.

[30] Foreign Application Priority Data

Jun. 20, 1988 [JP] Japan .................................. 63-81776
May 2, 1989 [JP] Japan .................................. 1-52271

[51] Int. Cl.$^5$ .......................................... G01N 29/04
[52] U.S. Cl. .......................................... 73/633; 73/606
[58] Field of Search .................. 73/606, 615, 633, 665; 250/306

[56] References Cited

U.S. PATENT DOCUMENTS 4,446,738 5/1984 Ishikawa et al. ................... 73/606
4,698,502 10/1987 Bednorz et al. ..................... 250/306

FOREIGN PATENT DOCUMENTS 0258162 11/1986 Japan .................................. 73/606
0259166 11/1986 Japan .................................. 73/606
0154962 6/1988 Japan .................................. 73/606

OTHER PUBLICATIONS

"Acoustic Microscopy at Less Than 0.2° K", Rugar et al, Acoustical Imaging, vol. 12, pp. 17–18, Jul. 19, 1982.

Primary Examiner—Hezron E. Williams
Assistant Examiner—Louis M. Arana
Attorney, Agent, or Firm—Armstrong, Nikaido, Marmelstein, Kubovcik & Murray

[57] ABSTRACT

A scanning apparatus for scanning which is used in a scanning microscope having an observation apparatus for observing a sample wherein the sample is secured in order to obtain an image of the same. The scanning apparatus includes a moving apparatus for moving at least either the sample or the observation apparatus in order to scan the sample, and a vibration attenuating element structurally provided for the moving apparatus for attenuating relative vibration between the sample and the observation.

8 Claims, 5 Drawing Sheets

SCANNING APPARATUS FOR A SCANNING MICROSCOPE

This application is a continuation of application Ser. No. 365,149 filed June 12, 1989, now abandoned.

BACKGROUND OF THE INVENTION

1. Field of the Invention

The present invention relates to a scanning apparatus for a scanning microscope, and particularly relates to a lens scanning apparatus for an ultrasonic microscope.

2. Related Art Statement

In recent years, an ultrasonic microscope has been put to practical use in which a sample to be observed is two-dimensionally scanned with an ultrasonic beam and reflected waves or transmitted waves from the sample are received to form an ultrasonic image of the sample. In the ultrasonic microscope, a sample should be scanned through relatively two-dimensional moving a lens and a sample. As such a scanning method, there are various methods including a method of scanning a lens in the X direction and scanning a sample in the Y direction, a method of scanning a lens and a sample in the X-Y direction and so on. Also, although there are various means for scanning a lens or a sample in the X-Y direction, one of such means is the X-Y scanner used for a low temperature ultrasonic microscope, shown on pages 17 and 18 in *Acoustical Imaging*, Vol. 12.

In this X-Y scanner, for example, a lens supporting stand for supporting a lens is fitted to a scanner supporting stand through a spring(tube). A coil is fitted to this lens supporting stand, but on the other hand, a magnet is fitted to the scanner supporting stand. By these coil and magnet, the lens supporting stand can be moved in the X-Y direction.

The above mentioned scanner has superior features in several points, but on the other hand, if the above mentioned spring is made to be inelastic so as to be able to drive the electric power as small as possible, the scanner is easily vibrated by a variation coming from the outside, by noise of a driving signal, by relative harmonic contents and so on. Such a variation becomes a deflection of the picture image and will remarkably reduces the quality of a picture. Therefore, an electrical counterplan such as a servomechanism, has been usually considered; however, the counterplan is not enough, especially for above mentioned several noises of a frequency near the resonance point.

OBJECT AND SUMMARY OF THE INVENTION

An object of the present invention is to provide a scanning apparatus for a scanning microscope wherein vibration can be reduced.

The scanning apparatus for the scanning microscope of the present invention is used in a scanning microscope having an observation device for observing a sample wherein the sample is scanned in order to obtain an image of the sample, and comprises a moving device for moving at least either the sample or the observation device in order to scan the sample and a vibration attenuating device structurally provided for the moving device for attenuating relative vibration between the sample and the observation device.

The other features and advantages of the present invention will become apparent in the following explanation.

BRIEF DESCRIPTION OF THE DRAWINGS

FIG. 1 is a sectioned view showing the X-Y scanner.

FIG. 2 is a part of a sectioned view showing the whole of a low temperature ultrasonic microscope.

DETAILED DESCRIPTION OF THE PREFERRED EMBODIMENTS

Figure 1:
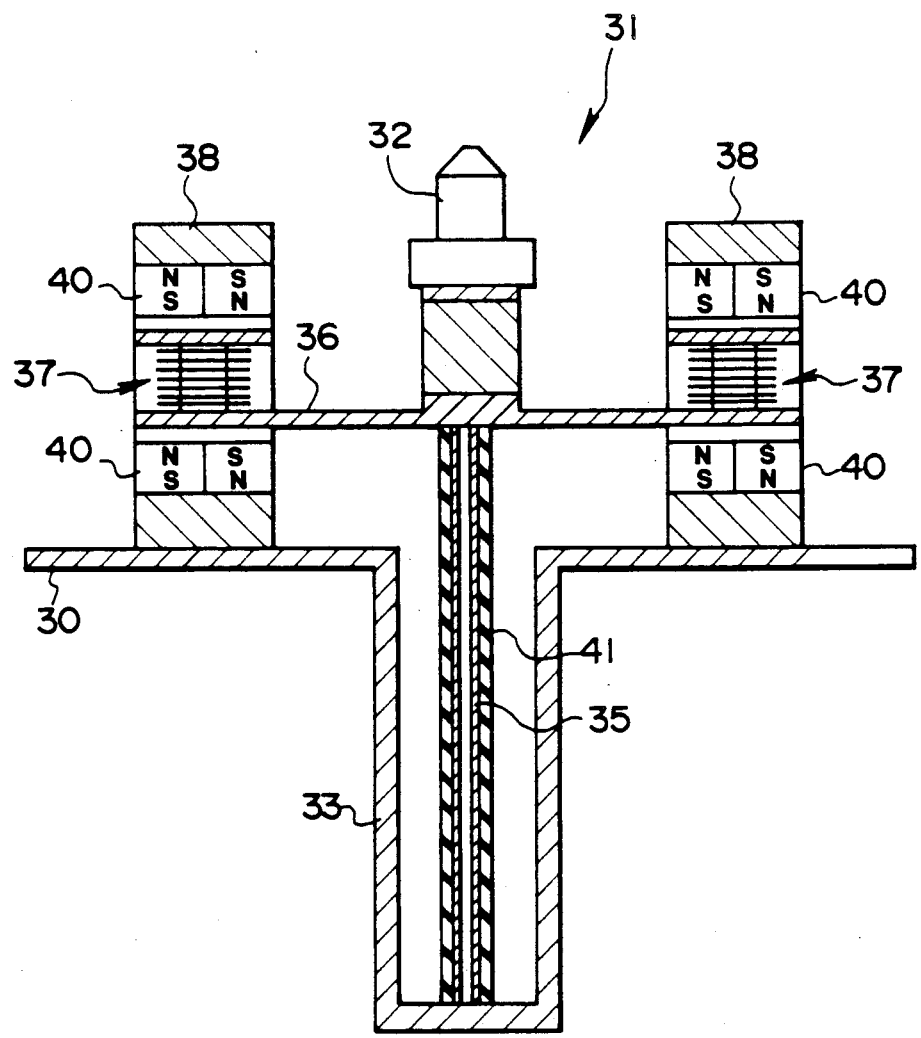
FIGS. 1 and 2 relate to the first embodiment of the present invention.
Figure 2:
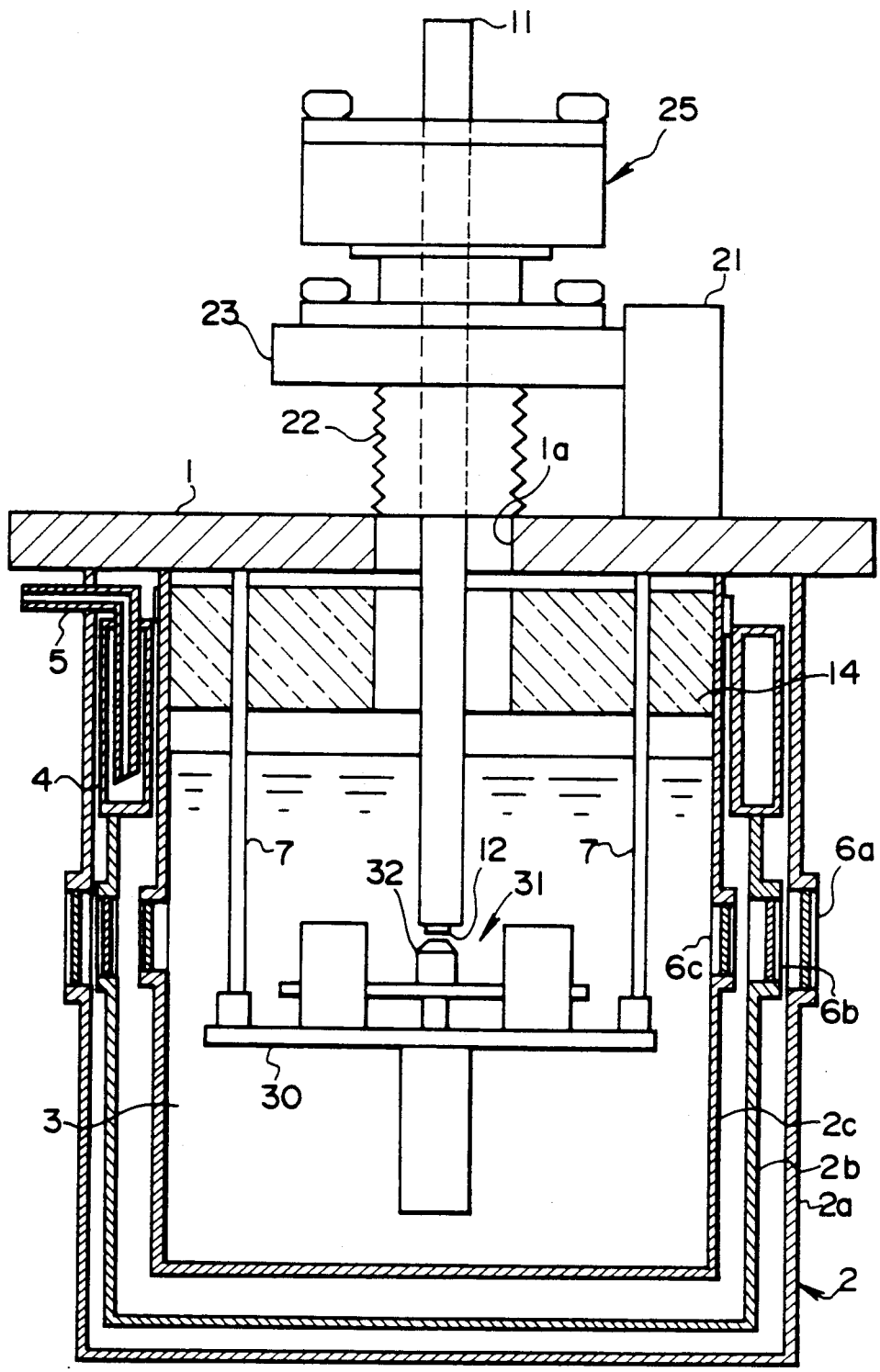

The first embodiment of the present invention is shown in FIGS. 1 and 2.

As shown in FIG. 2, the low temperature ultrasonic microscope applied to this embodiment has a base 1 below which a low temperature tank 2 as an adiabatic container is sealed and fitted. Liquid nitrogen 3 which is an ultrasonic wave transferring medium is contained in this low temperature tank 2 which is a double vacuum structure of triple containers 2a, 2b and 2c and within which an annular tank 4 is provided. A pipe 5 is led into the annular tank 4 through the outside container 2a so that liquid nitrogen may be enclosed through this pipe 5. The temperature elevating action from the outside is to be prevented by the annular tank 4 enclosing this liquid nitrogen. The respective side walls of the containers 2a, 2b and 2c of the above mentioned low temperature tank 2 are provided respectively with peep holes 6a, 6b and 6c through which the distance between the acoustic lens and sample can be confirmed from the outside.

The above mentioned base 1 has an opening 1a in the central part. Four scanner supports 7 are provided to project downward on the lower surface of the base 1 around this opening 1a. Only two scanner supports 7 are shown in FIG. 2. A scanner supporting stand 30 is fitted to the lower ends of these scanner supports 7. A X-Y scanner 31 is fitted to the scanner supporting stand 30 to which an acoustic lens 32 is fitted. This acoustic lens 32 is to be two-dimensional driven in an XY plane intersecting at right angles with a paper surface by the above mentioned X-Y scanner 31.

A sample rod 11 is inserted into the above mentioned low temperature tank 2 through the opening 1a of the above mentioned base 1 and is arranged in the Z direction upward of the above mentioned acoustic lens 32. A sample stand 12 is fitted to the lower end of this sample rod 11 and is to be fitted with a sample to be observed. The high frequency electric power generated from a transmitter (which is not shown in the figures) is converted to ultrasonic waves by a piezoelectric transducer bonded to the acoustic lens 32 through a circulator, which is also not shown in the figures. These ultrasonic waves are converged by the above mentioned acoustic lens 32 and the ultrasonic beam emitted from this acoustic lens 32 reaches the sampled through the liquid nitrogen 3 which is a transferring medium. Therefore, the sample will be two-dimensionally scanned by the ultrasonic beam. The reflected waves from the sample are concentrated by the above mentioned acoustic lens 32, are converted to an electric signal by the above mentioned piezoelectric transducer and this electric signal is converted to a picture signal by the above mentioned piezoelectric transducer and this electric signal is converted into a picture signal by a signal processing circuit through the above mentioned circulator and a signal processing circuit, which is not shown in figures. This picture signal is input into a monitor (which is not shown in the figures) in which an ultrasonic image is to be displayed.

The above mentioned sample rod 11 is formed of a hollow pipe, for example, of stainless steel. If the above mentioned sample rod 11 is formed of a material of the same thermal expansion coefficient of the scanner support 7, even if the liquid level of the liquid nitrogen 3 varies, the sample will be able to be prevented from being displayed in the Z direction with respect to the acoustic lens 32. An annular adiabatic member 14 is arranged near the opening of the above mentioned low temperature tank 2 to attain the adiabatic effect on the opening side.

On the other hand, an X-Y-Z stage 21 for moving the above mentioned sample rod 11 in X, Y and Z directions is fitted on the above mentioned base 1 and a bellows 22, through which the above mentioned sample rod 11 is inserted, is fitted on the upper surface of the base 1 around the opening 1a of the above mentioned base 1. A movable table 23 of the above mentioned X-Y-Z stage 21, in which the above mentioned sample rod 11 is inserted, is fitted on the upper end of this bellows 22. When the sample is observed, the sample rod 11 is moved in the directions of X, Y and Z by the X-Y-Z stage 21 so as to select observation parts and to adjust focus.

A sliding seal 25 is fitted on the upper surface of the above mentioned movable table 23 so as to airtightly seal the low temperature tank 2 and the outside, and to fix the above mentioned sample rod 11.

The X-Y scanner 31 of this embodiment is formed as shown in FIG. 1.

An opening is provided in the central part of the above mentioned scanner supporting stand 30 and a cylindrical body 33 in which the bottom is blocked is provided below the opening. On the upper surface of the bottom of this body 33, for example, a metallic supporting pipe 35, which functions as a spring facing upward, is provided. The upper part of this pipe 35 projects over the above mentioned scanner supporting stand 30 and a lens supporting stand 36 is provided on the upper end of the pipe 35. The above mentioned acoustic lens 32 is fitted on the lens supporting stand 36. On the upper surface of the outer circumference of the above mentioned lens supporting stand 36, a coil 37 is fitted. On the upper surface of the above mentioned scanner supporting stand 30, a yoke 38 is fitted as if the above mentioned coil 37 is put between the yoke 38 from the upper and lower sides. A magnet 40, which is opposing to the above mentioned coil 37 at a predetermined interval from the upper and lower sides, is fitted to the inside of the yoke 38. By applying an electric current to the above mentioned coil 37, the above mentioned lens supporting stand 36 moves in the X-Y direction by the power derived from the magnetic field based on the electric current of the coil 37 and the above mentioned magnet 40 so that the above mentioned acoustic lens 32 may scan the above mentioned sample 12 in the X-Y direction.

In this embodiment, gum 41 which is a damper material is affixed as a structural vibration attenuating means to the outer circumference of the above mentioned pipe 35 which functions as a spring for the above mentioned X-Y scanner 31 in order to reduce a Q value of resonance.

Thus, in the embodiment, since the structural vibration attenuating means through the gum 41 is provided in the X-Y scanner 31, the vibration coming from the outside, the vibration caused by the noise of the driving signal and the vibration caused by the higher harmonics contents of the driving signal and so on can be reduced. Accordingly, deflection of the picture image through the vibration can be prevented and it will become possible that the spring(pipe 35) is made to be inelastic so as to be able to drive by electric power as small as possible.

Furthermore, since it is not always necessary that the vibration attenuating means affixed to the pipe 35 should be gum, such as soft resin is suitable.

Figure 3:
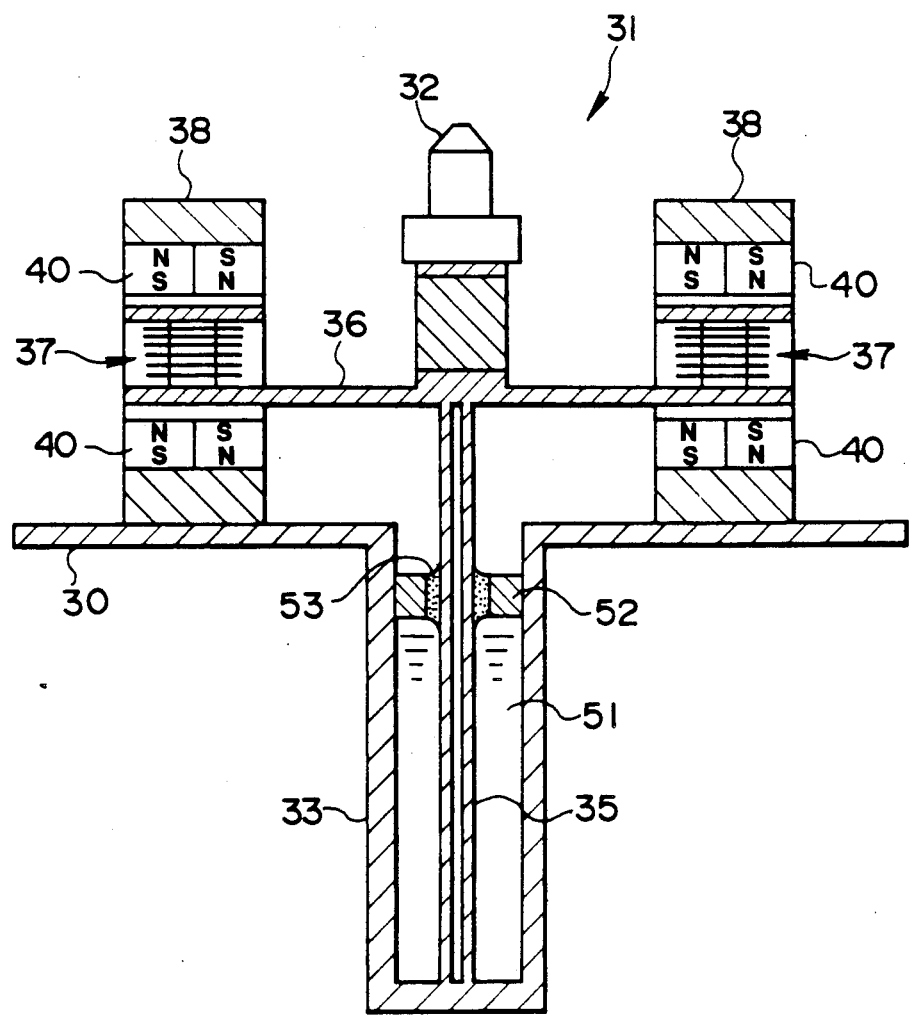
FIG. 3 is a sectioned view showing the X-Y scanner of the second embodiment of the present invention.

The second embodiment of the present invention is shown in FIG. 3.

In this embodiment, liquid 51, which is stable and has appropriate viscosity, a low steam pressure (for example, oil for a rotary pump) and low melting pint, is contained in the body 33 in which the pipe 35 functions as a spring of the X-Y scanner 31 is installed. The motion of the pipe 35 is applied damping by hydrodynamic friction(viscous drag) between the liquid 51 and the pipe 35 so that the vibration of the pipe 35 is attenuated by viscous damping.

It i not always necessary that the X-Y scanner 31 is used to turn the acoustic lens 32 upward as shown in the figures, and in some cases, the acoustic lens 32 is turned over upside down, and there are many cases that it is convenient to use the acoustic lens 32 so as to turn the lens downward. In this case, it is necessary to put on a lid of small resistance so that the liquid 51 may not flow out and the movement of the pipe 35 may not be disturbed. Then, in this embodiment, a ring magnet 52 is fitted to the inner circumference of the opening of the body 33, and magnetic fluid 53 is fitted between the inner circumference of the ring magnet 52 and the above mentioned pipe 35 so that the inner circumference is closed by the magnetic fluid 53.

The others are of the same formation, operations and effects as in the first embodiment.

Figure 4:
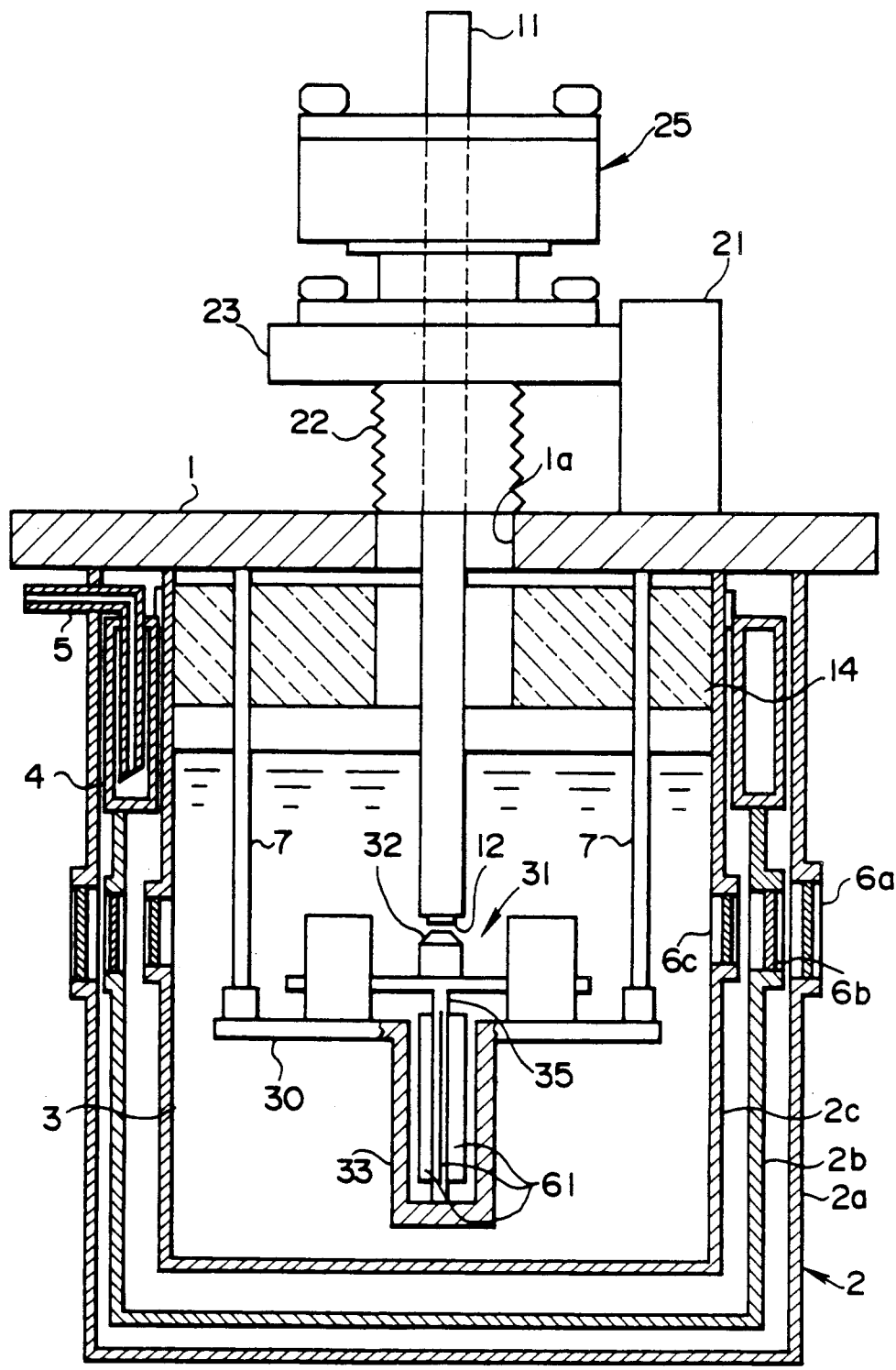
FIG. 4 is a part of a sectioned view showing the entire low temperature ultrasonic microscope of the third embodiment of the present invention.

The third embodiment of the present invention is shown in FIG. 4.

In the first embodiment, the gum 41 is affixed as a damper material to the supporting pipe 35 which fills the role of a spring for the X-Y scanner 31; however, in this embodiment, a plurality of wings(or fins) 61 are fitted to the above mentioned supporting pipe 35 in place of the gum 41, and the wings 61 are projecting in the cooling liquid(liquid nitrogen 3) around the supporting pipe 35.

In this embodiment, the motion of the pipe 35 fitted with the above mentioned wings 61 is applied damping by the viscous drag for the wings 61 in the above mentioned cooling liquid so that the vibration of the pipe 35 is attenuated by the viscous damping.

The others are of the same formation, operations and effects as in the first embodiment.

Figure 5:
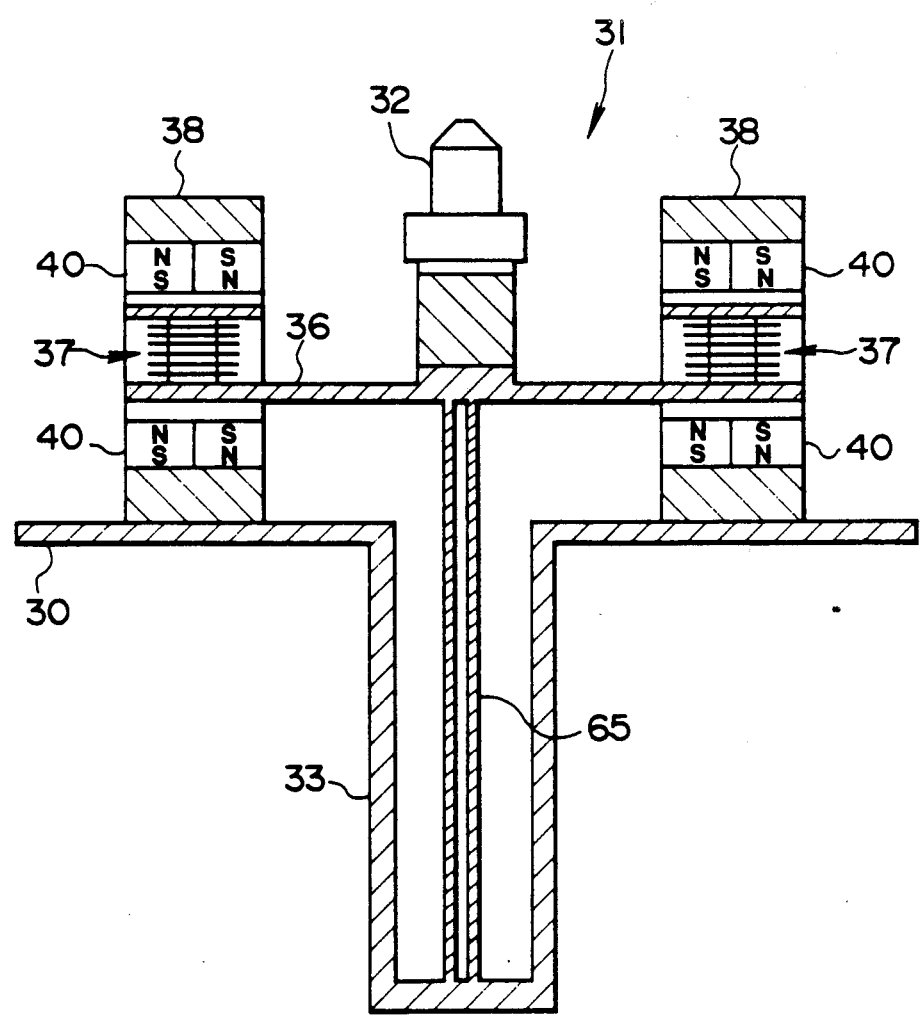
FIG. 5 is a sectioned view showing the X-Y scanner of the fourth embodiment of the present invention.

The fourth embodiment of the present invention is shown in FIG. 5.

In this embodiment, a supporting pipe 65 composed of a nonresonance alloy(such as the product name of SILENTALLOY of Toshiba, Inc.) as a material is provided instead of the supporting pipe 35 on which the gum 41 is affixed in the first embodiment. That is to say, this embodiment supplies the supporting pipe 65 with a damping effect by the material itself.

The others are of the same formation, operations and effects as in the first embodiment.

Further, the present invention is not restricted by the above each embodiment. For example, the scanning apparatus may also scan by moving a sample and without moving a lens. The present invention can be also applied to a transmission type ultrasonic microscope in which ultrasonic waves have passed through the sample during the waves are dispersing and attenuating and are converted into picture images.

Also, the present invention can be applied not only to an ultrasonic microscope but also to a scanning apparatus of a microscope wherein scanning is needed. Furthermore, besides microscopes, the present invention can be applied to a mechanical scanning apparatus such as an ultrasonic diagnostic apparatus and an ultrasonic endoscope.

As explained above, according to the present invention, there are effects that a vibration can be attenuated because a structural vibration attenuating means is provided in a scanning apparatus for the scanning microscope.

It is apparent that, in this invention, working modes different in a wide range can be formed on the basis of this invention without departing from the spirit and scope of the invention. This invention is not restricted by its specific working modes except being limited by the appended claims.

What is claimed is:

1. A scanning apparatus for ultrasonic scanning used in an ultrasonic scanning microscope having an observation means for acoustically observing a sample, said observation means including an acoustic lens projecting an ultrasonic beam onto said sample and receiving an acoustic wave distributed by said sample, wherein said sample is scanned in order to obtain an image of said sample, said scanning apparatus comprising:
    a moving means for moving at least either said sample or said observation means in order to scan said sample, said moving means including a spring element which elastically supports at least one of said sample and said observation means; and
    a vibration attenuating means, structurally provided for said moving means, for attenuating relative vibration in a moving direction of said moving means between said sample and said observation means, said vibration attenuating means provided separately from said spring element.

2. A scanning apparatus of claim 1 wherein said vibration attenuating means includes damping materials fitted to said spring element of said moving means.

3. A scanning apparatus of claim 1 wherein said vibration attenuating means includes fluid having viscosity provided around said spring element of said moving means so that a vibration of said spring element is attenuated by a viscous damping based on the movement of said spring element in said fluid.

4. A scanning apparatus of claim 1 wherein said vibration attenuating means includes fluid having viscosity provided around said spring element of said moving means and a fin provided in said spring element of said moving means moving in said fluid so that a vibration of said spring element is attenuated by a viscous damping based on said fin's movement in said fluid.

5. A scanning apparatus of claim 1 wherein said moving means moves said observation means.

6. A scanning apparatus of claim 1 wherein said moving means moves said acoustic lens.

7. A scanning apparatus of claim 1 wherein said scanning microscope has cold liquid being an ultrasonic transferring medium wherein said sample and said acoustic lens are inserted, and said vibration attenuating means includes a fin provided in said spring element of said moving means moving in said cold liquid so that a vibration of said spring element is attenuated by a viscous damping based on said fin's movement in said cold liquid.

8. A scanning apparatus for ultrasonic scanning used in an ultrasonic scanning microscope having an observation means for acoustically observing a sample, said observation means including an acoustic lens projecting an ultrasonic beam onto said sample and receiving an acoustic wave distributed by said sample, wherein said sample is scanned in order to obtain an image of said sample, said scanning apparatus comprising:
    a moving means for moving at least either said sample or said observation means in order to scan sample, said moving means including a supporting member, being composed of nonresonance materials, for elastically supporting at least either said sample or said observation means so that relative vibration in a moving direction of said moving means between said sample and said observation means is attenuated by a damping effect by said supporting member itself.

* * * * *